United States Patent [19]

Dedo

[11] Patent Number: 4,820,279
[45] Date of Patent: Apr. 11, 1989

[54] ARTICLE AND METHOD FOR PREPPING A PATIENT PRIOR TO SURGERY

[76] Inventor: Richard G. Dedo, 175 Denise Dr., Hillsborough, Calif. 94010

[21] Appl. No.: 846,147

[22] Filed: Mar. 31, 1986

[51] Int. Cl.⁴ ............................................. A61M 35/00
[52] U.S. Cl. ...................................... 604/290; 128/155
[58] Field of Search ................. 604/290; 128/155, 156

[56] References Cited

U.S. PATENT DOCUMENTS

| 2,077,299 | 4/1937 | Abrams | 128/156 |
|---|---|---|---|
| 2,082,599 | 6/1937 | Sawyer | 128/156 |
| 2,529,139 | 11/1950 | Corbett | 128/156 |
| 3,097,644 | 7/1963 | Parker | 128/156 |
| 3,263,682 | 8/1966 | Rosenfield | 128/156 |
| 3,367,332 | 2/1968 | Groves | 604/270 |
| 3,439,676 | 4/1969 | Burda | 604/290 |
| 3,548,820 | 12/1970 | Bergen | 128/156 |
| 3,556,871 | 3/1971 | Richter et al. | 128/156 |
| 3,805,781 | 4/1974 | Hoey | 128/156 |
| 4,310,509 | 1/1982 | Berglund | 128/155 |
| 4,466,431 | 8/1984 | Tharrat et al. | 128/155 |
| 4,608,044 | 8/1986 | Nordqvist et al. | 128/156 |
| 4,617,326 | 10/1986 | Bjornberg et al. | 128/156 |
| 4,638,796 | 1/1987 | Sims | 128/155 |
| 4,643,179 | 2/1987 | Wang | 128/155 |

Primary Examiner—C. Fred Rosenbaum
Assistant Examiner—Mark F. Colosimo
Attorney, Agent, or Firm—Emrich & Dithmar

[57] ABSTRACT

A method of prepping the skin of a patient in preparation for surgery, comprising the steps of covering the skin in the region of the site of surgery with a material retaining sufficient bactericidal agent to apply continuously the agent to the skin, covering the retaining material with a liquid and bacteria impervious material, maintaining the skin in the covered condition for a prolonged period of time, and removing the retaining and liquid impervious materials prior to surgery.

31 Claims, 4 Drawing Sheets

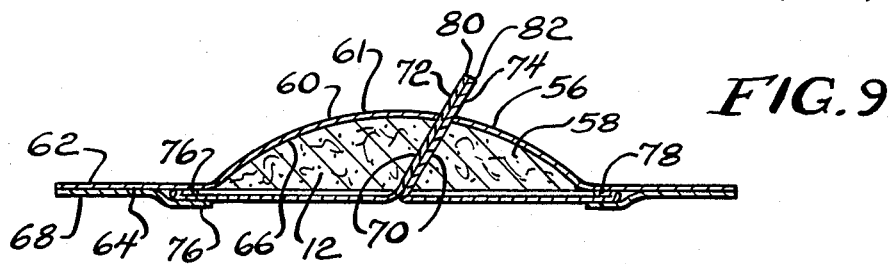
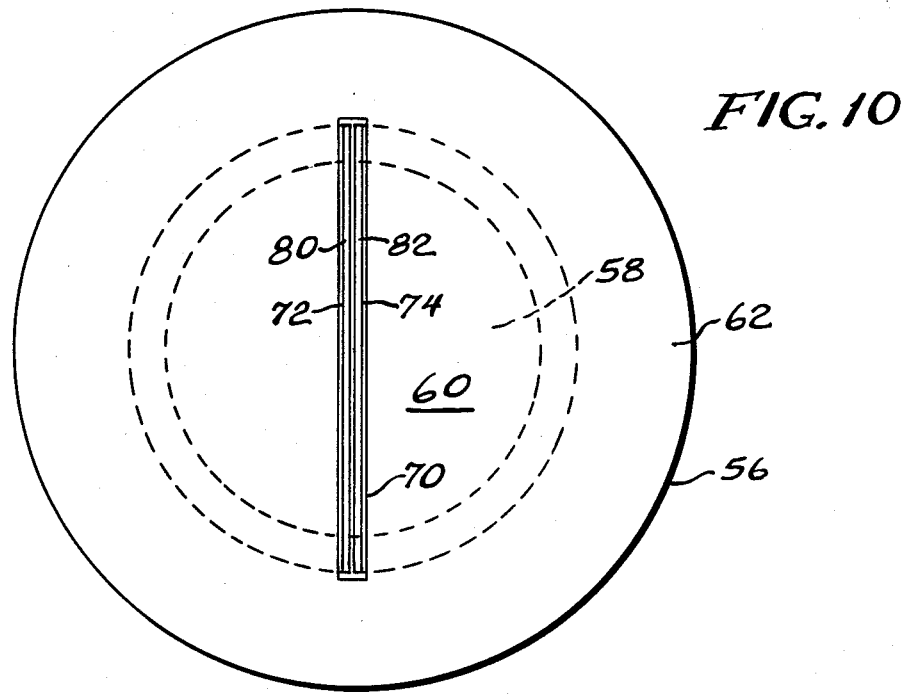
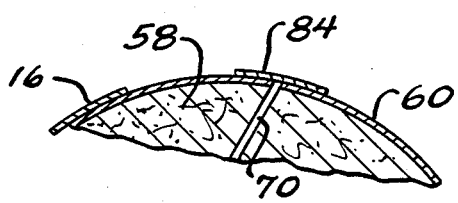
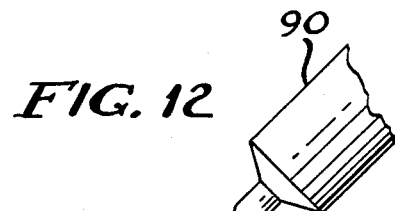
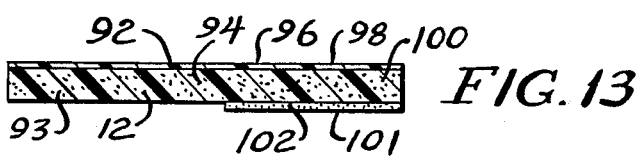

U.S. Patent  Apr. 11, 1989  Sheet 4 of 4  4,820,279
FIG. 14
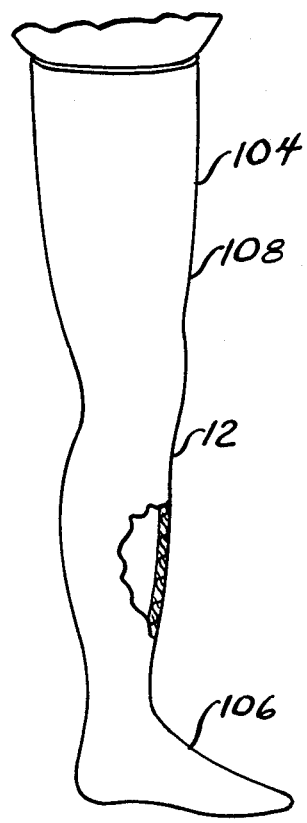
FIG. 15
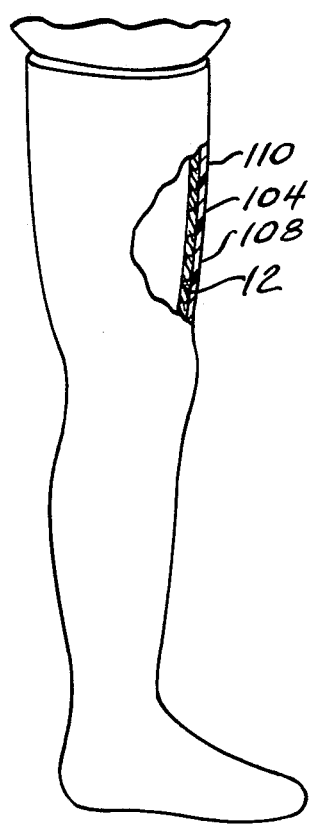
FIG. 17
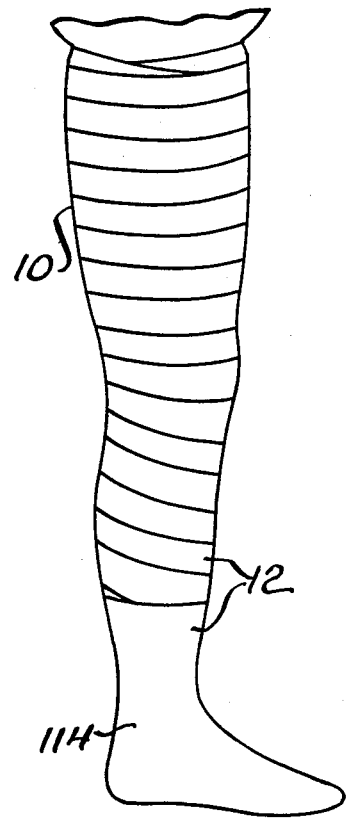
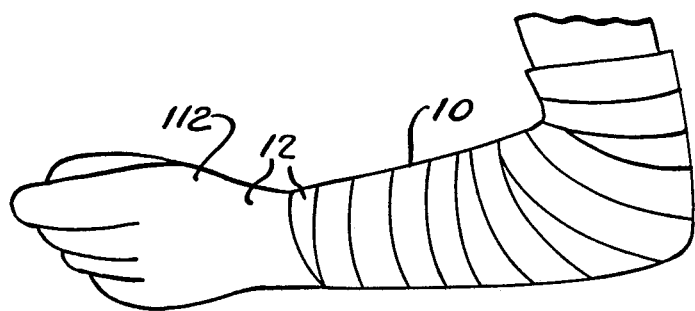
FIG. 16
FIG. 18
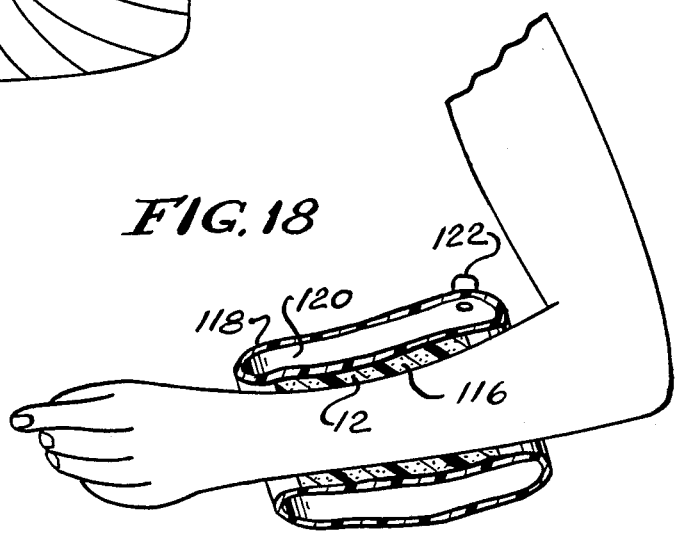

ARTICLE AND METHOD FOR PREPPING A PATIENT PRIOR TO SURGERY

BACKGROUND OF THE INVENTION

The present invention relates to articles and methods for prepping a patient prior to surgery.

Prior to surgery, the present technique for prepping a patient comprises a ten-minute surgical scrub using a soap and/or a bactericidal agent, usually in the operating room. In spite of this and other precautions, it has been found that bacteria from the skin cause subsequent superficial and deep wound infections in a certain number of the surgical cases, which of course is undesirable. It is believed that such bacteria come from the sebaceous ducts and glands, the sweat glands, from the outer dead keratinized layer of the skin, and from the environment.

The result of such skin infections can be very serious to the patient. For example, in a total hip operation, in the case of infection it is necessary to bring the patient back into the hospital to treat the infection, and later re-admit the patient to replace the total hip at a cost of at least $20,000. Further, a surgical infection has deleterious effects on a patient, including those associated with the trauma of repeat surgical procedures, exposure to nosicomial infection(s), septicemia, and death.

The present prepping procedures also require undue time spent in the operating room which delays the surgical procedure and prolongs anesthetic time. When considering the approximately 20,000,000 surgical procedures in the United States each year, it will be seen that the total time delay in the operating room due to the current prepping procedures is enormous, not to mention the total cost of the prepping procedures which is approximately $300.00 for each prepping procedure. Hence, not only is it desirable to decrease the incidence of infections from the skin during surgical procedures, it is also desirable to eliminate the delays and costs associated with current prepping procedures in the operating room.

SUMMARY OF THE INVENTION

The present invention relates to prepping methods and articles to reduce the incidence of superficial and deep wound infection from the skin of a patient and from the environment.

The method of prepping the skin prior to surgery comprises the steps of covering the skin in the region of the site of surgery with a material retaining a bactericidal agent, covering the retaining material with a liquid impervious material, maintaining the skin in the covered condition for a prolonged period of time, and removing the retaining and liquid impervious materials prior to surgery.

A feature of the present invention is that the skin is maintained in the covered condition preferably for longer than six hours before surgery.

Another feature of the invention is that the retaining material is sufficiently saturated to apply continuously the bactericidal agent to the skin.

Still another feature of the invention is that the liquid impervious material serves as a barrier over the retaining material.

A feature of the invention is that the liquid impervious material is impervious to passage of bacteria to isolate the area of surgery from environmental contaminants.

Yet another feature of the invention is that the liquid impervious material raises the skin temperature of the patient.

A further feature of the invention is that the covering materials soften and hydrate the skin of the patient, allowing penetration by the bactericidal agent.

Another feature of the invention is that the covering materials stimulate the production of sebum and sweat by the patient.

Still another feature of the invention is that the liquid impervious material is preferably elastic to apply pressure against the retaining material and skin.

A feature of the invention is that the method minimizes the incidence of infection due to skin bacteria.

Still another feature of the invention is that the method significantly reduces delays and costs associated with conventional prepping techniques in the operating room.

A feature of the invention is the provision of methods for wrapping the coverings by elongated materials disposed on rolls.

Another feature of the invention is the provision of articles for covering various regions of the patient's body.

Further features will become more fully apparent in the following description of the embodiments of this invention and from the appended claims.

DESCRIPTION OF THE DRAWINGS

In the drawings:

FIG. 9 is a sectional view of a bandage for the patient;

FIG. 10 is a top plan view of the bandage of FIG. 9;

FIG. 11 is a fragmentary sectional view of the bandage of FIG. 10 after removal of cover sheets;

FIG. 12 is an elevational view, taken partly in section, showing the impregnation of a pad with a bactericidal agent according to a method of the present invention;

FIG. 13 is a sectional view of a wrap of the present invention;

FIG. 14 is a fragmentary elevational view of a stocking for the patient;

FIG. 15 is a fragmentary elevational view of another embodiment of the stocking for the patient;

FIG. 16 is an elevational view of a covering for the patient;

FIG. 17 is an elevational view of another embodiment of a covering for the patient; and FIG. 18 is a sectional view of a covering for the patient.

DESCRIPTION OF THE PREFERRED EMBODIMENTS

Figure 1:
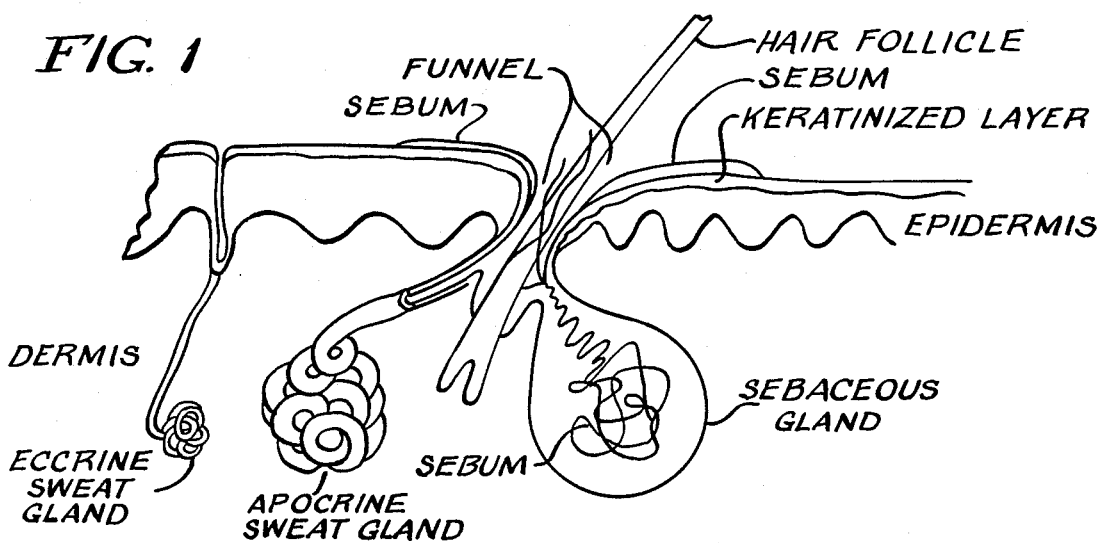
FIG. 1 is a diagrammatic view of a cross section of the skin.

Referring now to FIG. 1, there is shown a cross section of the skin which will be described to obtain a better understanding of the invention. As shown, the epidermis of the skin includes an outer keratinized layer which comprises dead cells which are stuck together. The skin has a hair follicle which is constructed from the same material as the keratinized layer, but is much more compact. Each of the hair follicles has an associated sebaceous gland which produces sebum, and the sebum flows from the sebaceous gland into a funnel surrounding the base of the hair and along the hair follicle onto the skin. Some hairs have apocrine sweat glands that empty into the funnels of the hair follicles; these specialized sweat glands harbor potentially pathogenic organisms. Additionally, eccrine sweat glands draining directly onto the skin harbor pathogenic organisms. It has been found that transient and resident bacteria live in the keratinized layer and in the sebaceous gland.

Figure 2:
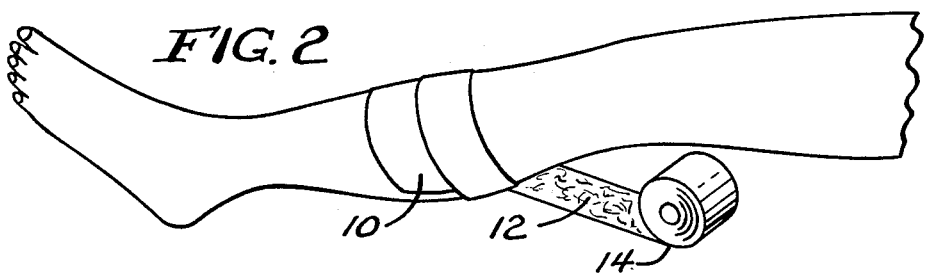
FIGS. 2 and 3 are perspective views illustrating the wrapping of a patient according to a method of the invention.

As shown in FIG. 2, according to a method of the invention, the patient's skin, in this case the extremity, is wrapped with an elongated sheet 10 of porous material, such as open cell foam or wadding, in the region of and over the surgical site, with the sheet 10 being saturated with sufficient semi-liquid or liquid bactericidal agent 12, such as povidone iodine, to apply the agent to the skin. As shown, the sheet 10 is unwound from a roll 14 of the porous material to facilitate wrapping of the skin.

Figure 3:
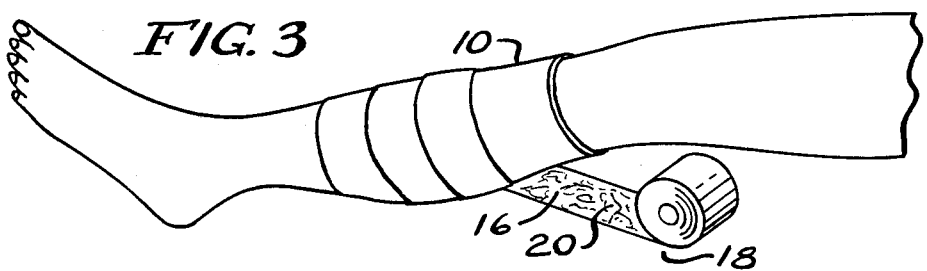

After wrapping by the sheet 10 has been completed, as shown in FIG. 3 an elongated sheet 16 of two-way elastic liquid and bacteria impervious material, such as silicone rubber, is wrapped over the agent retaining material 10 in a manner applying pressure by the sheet 16 against the underlying wrapped sheet 10. The sheet 16 is unwound from a roll 18 to facilitate the wrapping procedure, and the underlying sheet 10 is completely covered by the wrapped sheet 16. The sheet 16 preferably contains adhesive 20 on a front surface thereof in order to adhere the outer sheet 16 over the underlying sheet 10.

Once wrapping with the sheet 16 has been completed, the sheet 16 provides a liquid impervious barrier over the sheet 10 to prevent messiness associated with the bactericidal agent 12 on the sheet 10. The sheet 16 is impervious to passage of bacteria, and isolates the area of surgery from environmental contaminants, including antibiotic-resistant pathogenic organisms found in hospitals and in/on hospital personnel, as well as in/on the patient. The liquid impervious sheet 16 also cuts off the oxygen supply to aerobic bacteria which require oxygen to live. The pressure applied by the outer elastic sheet 16 forces the bactericidal agent 12 into the funnel associated with the hair follicle in order to kill bacteria in this region. Liquids will not normally enter the funnel by capillary action due to air in the funnel. The outer liquid impervious sheet 16 also raises the skin temperature of the patient beneath the sheet 16 to cause outward flow of sebum along the hair follicle and sweat onto the skin in order to expose the bacteria in this sebum and sweat to the bactericidal agent 12, and kill the bacteria. The outer elastic liquid impervious sheet 16 hydrates the keratinized layer of the patient beneath the sheet 16. The keratinized layer swells, becomes softer, and the bactericidal agent enters the keratinized layer over a period of time in order to kill bacteria in the keratinized layer. In this manner, the method of the present invention renders the skin substantially free of bacteria which otherwise could cause superficial and/or deep wound infection.

In order to accomplish this result, it is necessary to maintain the skin in the wrapped condition for prolonged periods of time before the surgical procedure. The skin should remain wrapped for longer than six hours, and preferably in the range of eight to as long as twenty-four hours. After being wrapped for a sufficient length of time, the patient is moved to the operating room where the wrapped sheets 10 and 16 are removed from the skin to expose the surgical site in a substantially bacteria free condition for the surgical procedure.

Figure 4:
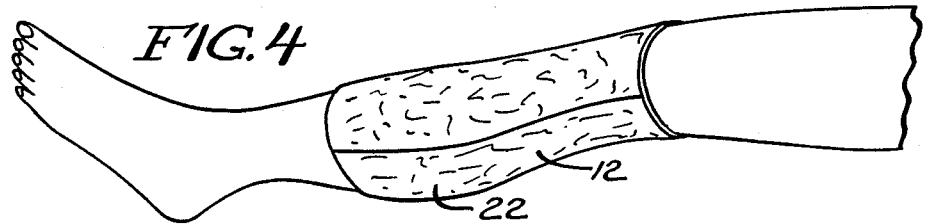
FIGS. 4 and 5 are perspective views illustrating the covering of a patient according to a method of the invention.
Figure 5:
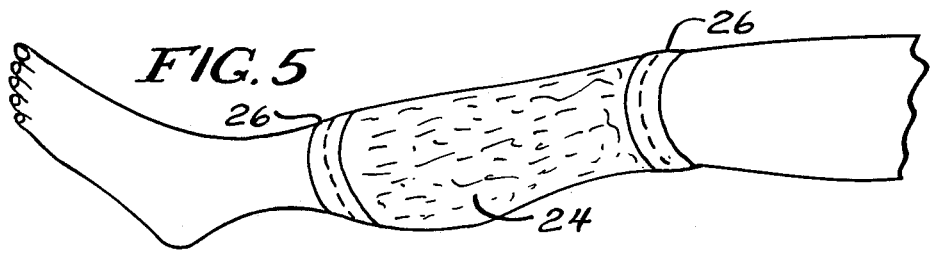

With reference to FIG. 4, according to a method of the invention, a large area of skin in the region of the surgical site may be covered with a porous pad 22, such as open cell foam, saturated with the bactericidal agent 12 in order to apply the agent to the skin. With reference to FIG. 5, the pad 22 is covered by a sheet 24 of two-way elastic liquid impervious material, such as silicone rubber, while applying pressure by the sheet 24 against the pad 22. The sheet 24 may be secured over the pad 22 by suitable tape strips 26 adjacent ends of the covering sheet 24. The materials are maintained in the covered condition for a prolonged period of time, such as longer than six hours prior to surgery, after which the materials are removed prior to surgery at the site. The results previously accomplished by the method described in connection with FIGS. 1 and 2 are also accomplished by the method described in connection with FIGS. 4 and 5.

Figure 6:
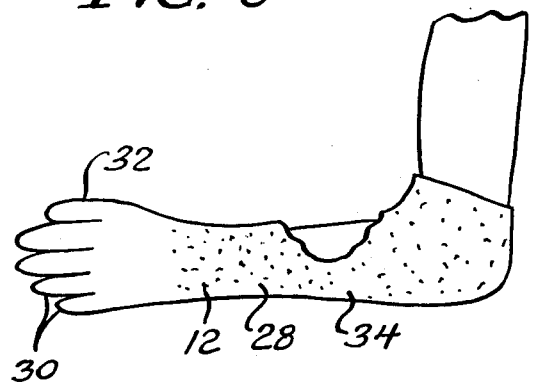
FIG. 6 is a fragmentary elevational view of a glove for a patient.
Figure 7:
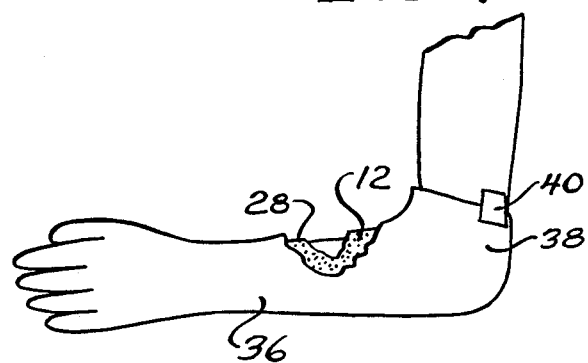
FIG. 7 is a fragmentary elevational view of another embodiment of the glove for the patient.

A hollow glove 28 of the present invention is illustrated in FIG. 6 for use in conjunction with the methods of the present invention. The glove 28 is constructed from a porous material, such as open cell foam, which is saturated with the bactericidal agent 12. The glove 28 may have finger portions 30 and a thumb portion 32 to receive the patient's fingers and thumb, and a hollow proximal portion 34 which covers the patient's arm preferably to a location well above the elbow. The glove 28 applies and maintains the bactericidal agent against the patient's skin, and the glove 28 may be wrapped with the elastic liquid impervious sheet 16 discussed in connection with FIG. 3 to cover the glove 28 and apply pressure against the glove 28 for a prolonged period of time. In FIG. 7, there is shown an outer glove 36 of elastic liquid impervious material, such as silicone rubber, which is utilized to cover the inner glove 28, and apply pressure by the outer glove 36 against the inner glove 28. The proximal end 38 of the glove 36 may be closed by a suitable tape strip 40. The gloves of FIGS. 6 and 7 may be utilized to kill skin bacteria beneath the gloves in a manner as previously described.

Figure 8:
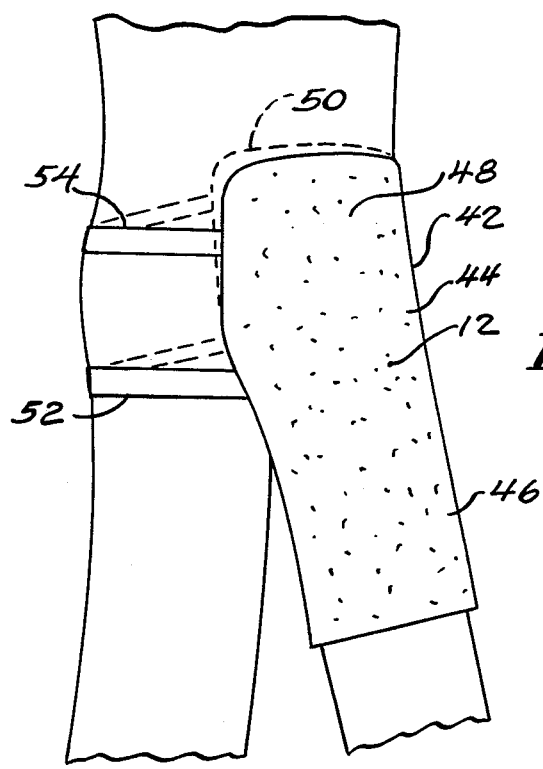
FIG. 8 is an elevational view of a pad for use over a hip of the patient.

An article 42 for use in conjunction with a total hip operation is illustrated in FIG. 8. The article 42 has a porous pad 44, such as open cell foam, having a lower tubular portion 46 which extends from the crotch of the patient along the leg preferably to the region of the mid thigh. The pad 44 extends upwardly from the tubular portion 46, and has a front panel 48 and a rear connected panel 50 sufficient in breadth to cover the patient's hip. The pad 44 is saturated with the bactericidal agent 12 to apply the agent to the skin in the region of the hip. The article 42 may have a pair of elastic straps 52 and 54 extending between the edges of the front and rear panels 48 and 50 to retain the pad 44 in place over the hip. The pad 44 is covered with an elastic liquid impervious sheet, such as silicone rubber, while applying pressure against the pad 44 for purposes described above, and the pad is maintained in the hip covering position for a prolonged period of time to kill bacteria according to the described methods of the invention.

The substantial elimination of infections by skin bacteria according to the skin prepping method of the present invention prevents complications caused by such infections. Further, the method eliminates the necessity of possible further surgery to treat a wound infection caused by skin organisms. For example, in total hip joint replacement surgery, the prosthetic device may need to be removed, the infection treated, and the prosthesis replaced, at a cost of at least $20,000. The invention has also eliminated the necessity for the expensive and time consuming scrub procedures in the operating room, thus reducing the time required in the operating room which is substantial when considering that 20,000,000 surgical procedures are performed in the United States each year. The method protects against pre-operative exposure to potentially pathogenic (hospital/hospital personnel/patient/environmental) organisms.

A bandage 56 of the present invention is illustrated in FIGS. 9-11 for use in conjunction with the methods of the present invention. The bandage 56 has a circular porous pad 58 which has its greatest thickness in the center of the pad 58, and which taper from the center of the pad 58 toward its edges. The bandage 56 has a bacteria and liquid impervious backing 60 covering a rear surface 61 of the pad 58, and having an edge section 62 extending beyond edges of the pad 58 peripherally around the pad 58. The backing 60 has an adhesive 64 on a front surface 66 of the backing 60 in order to secure the backing 60 onto the rear surface 61 of the pad 58, and secure the edge section 62 onto the skin. The bandage 56 has an annular release sheet 68 of suitable material releasably attached to the adhesive 64 on the edge section 62 in order to protect the adhesive 64 prior to use of the bandage 56.

The bandage 56 has an oblique slit 70 extending through a central portion of the pad 58 and backing 60, and extending at least the width of the pad 58. The bandage 56 has a pair of cover sheets 72 and 74 having inner ends 76 and 78 reverse folded and releasably secured to the adhesive 64 on the edge section 62, and outer ends 80 and 82 extending through the pad 58 and backing 60 to the outside of the bandage 56. The pad 58 is dripping wet with a bactericidal agent 12, and the cover sheets 72 and 74 prevent leakage of the agent from the pad 58 prior to use of the bandage 56.

In use, the release sheet 68 is removed from the bandage 56, and the edge section 62 is secured to the patient with the pad 58 located over the site of surgery. Next, the outer ends 80 and 82 of the cover sheets 72 and 74 are pulled in order to peel the inner ends 76 and 78 from the adhesive 64, and remove the cover sheets 72 and 74 from the bandage 56 through the slit 70, thus exposing the pad 58 to the patient's skin without loss of the bactericidal agent from the pad 58, since the pad 58 is exposed after securement of the bandage 56. Since the slit 70 is oblique, all parts of the skin under the pad 58 are covered by the pad 58. In a preferred form, the backing 60 is constructed from an elastic material, such as silicone rubber, such that the backing 60 causes pressure to be applied by the pad 58 according to the methods of the present invention. The tapered shape of the pad 58 causes more pressure to be applied by the central portion of the pad 58 than the side portions of the pad 58.

After removal of the cover sheets 72 and 74 from the bandage 56, the outer end of the slit 70 is covered by a bacteria impervious tape strip 84 in order to prevent passage of bacteria through the slit 70. In the event that the backing 60 is not elastic, the secured bandage may be wrapped with an elastic sheet 16 to apply pressure against the pad 58.

A bandage 56 for use in accordance with a method of the present invention is illustrated in FIG. 12, in which like reference numerals designate like parts. In this embodiment, the bandage 56 is free of a slit and cover sheets, and has a dry pad 58. After removal of the release sheet 68, and securement of the edge section 62 to the patient's skin, the tip 86 of a needle 88 attached to a syringe 90 is passed through the backing 60 into the pad 58, and the syringe 90 is pumped in order to eject a liquid bactericidal agent through the needle and into the pad in order to saturate the pad with the agent, after which the needle 88 is removed from the bandage 56. The elastic backing 60 applies pressure to the pad 58 in order to carry out the methods of the present invention.

A wrap 92 for use in practicing the methods of the invention is illustrated in FIG. 13. The wrap 92 comprises an elongated sheet 93 constructed from a suitable elastic foam 94, such as open cell polyurethane foam, which is saturated with a liquid bactericidal agent 12. The foam 94 has a liquid and bacteria impervious rear skin 96 defining a back surface 98 of the foam 94 in order to prevent passage of the agent to the back surface 98, and provide a barrier for the foam 94. A side portion 100 of the foam 94 has a suitable adhesive 101 on a front surface 102 of the side portion 100. In a suitable form, the adhesive-covered side portion 100 may constitute about one-third of the width of the wrap 92.

In use, the wrap 92 is first wrapped one turn on the patient such that the adhesive 101 secures the wrap 92 to the skin, and after the first wrapped turn of the wrap 92, the adhesive 101 of the wrap 92 is secured over the rear surface of the previous wrapped turn. Since the foam 94 is elastic, the sheet 93 when wrapped applies pressure to the patient's skin, and the rear skin 96 of the wrap 92 serves as a liquid and bacteria impervious barrier in order to accomplish the methods of the present invention.

A hollow stocking 104 of the present invention is illustrated in FIG. 14 for use in conjunction with the methods of the present invention. The stocking 104 is constructed from a porous material, such as open cell foam, which is saturated with the bactericidal agent 12. The stocking 104 has a first portion 106 to cover the patient's foot, and a hollow proximal boot portion 108 which covers the patient's leg preferably to a location adjacent to the groin. The stocking 104 applies and maintains the bactericidal agent against the patient's skin, and the stocking 104 may be wrapped with the elastic liquid impervious sheet discussed in connection with FIG. 3 to cover the stocking 104 and apply pressure against the stocking 104 for a prolonged period of time. In FIG. 15, there is shown an outer stocking 110 of elastic liquid and bacteria impervious material, such as silicone rubber, which is utilized to cover the inner stocking 104, and apply pressure by the outer stocking 110 against the inner stocking 104. The stockings of FIGS. 14 and 15 may be utilized to kill skin bacteria beneath the stockings in a manner as previously described.

A covering for the arm of a patient is illustrated in FIG. 16. First, a hollow porous glove 112 of the general type disclosed in FIG. 6 is utilized to cover the patient's hand, and extends to a location on the arm below the level of surgery. The remaining part of the arm is wrapped by a porous sheet 10 to a location above the elbow. The glove 112 and sheet 10 are saturated with a liquid bactericidal agent 12, and the impregnated glove 112 and sheet 10 may be wrapped with the elastic liquid and bacteria impervious sheet 16 as discussed in connection with FIG. 6, or with the elastic outer glove as discussed in connection with FIG. 7 in order to perform the methods of the present invention.

A covering for the leg of a patient is illustrated in FIG. 17. First, a hollow porous stocking 114 of the general type disclosed in FIG. 14 is utilized to cover the patient's foot, and extends to a location on the leg below the level of surgery. The remaining part of the leg is wrapped by a porous sheet 10 to a location adjacent to the groin. The stocking 114 and sheet 10 are saturated with a liquid bactericidal agent 12, and the impregnated stocking 114 and sheet 10 may be wrapped with the elastic liquid and bacteria impervious sheet 16 as discussed in connection with FIG. 14, or with the elastic outer stocking as discussed in connection with FIG. 15 in order to perform the methods of the present invention.

A covering of the present invention is illustrated in FIG. 18. The covering has an inner porous pad or wrap 116 saturated with a bactericidal agent 12 and positioned over the site of surgery, such as on an extremity. The covering has an outer hollow inflatable sleeve 118 having a chamber 120. The sleeve 118 is positioned over the pad or wrap 116, and the sleeve 118 is inflated through a valve 122 of known type, such that the sleeve 118 applies pressure against the inner pad or wrap 116 in order to perform the methods of the present invention.

The foregoing detailed description is given for clearness of understanding only, and no unnecessary limitations should be understood therefrom, as modifications will be obvious to those skilled in the art.

I claim:

1. A method of prepping the skin of a patient prior to surgery, comprising the steps of:
    covering the skin in the region of the site of surgery with a material retaining sufficient bactericidal agent to apply the agent to the skin;
    covering the retaining material with a liquid and bacteria impervious material;
    maintaining the skin in the covered condition for a prolonged period of time; and
    removing the retaining and liquid impervious materials prior to surgery.

2. The method of claim 1 wherein the maintaining step comprises the step of maintaining the covered condition for longer than six hours.

3. The method of claim 1 wherein the second covering step includes the step of applying pressure by the liquid impervious material against the retaining material.

4. The method of claim 1 wherein the second covering step includes the step of raising the skin temperature of the patient beneath the covering materials.

5. The method of claim 1 including the step of hydrating the skin of the patient beneath the covering materials.

6. The method of claim 1 including the step of stimulating the production of sebum and sweat in the patient beneath the covering materials.

7. A method of prepping the skin of a patient prior to surgery, comprising the steps of:
    covering the skin in the region of the site of surgery with a material retaining sufficient bactericidal agent to apply the agent to the skin;
    covering the retaining material with an elastic liquid and bacteria impervious material while applying pressure against the retaining material;
    maintaining the skin in the covered condition for a prolonged period of time; and
    removing the retaining and liquid impervious materials prior to surgery.

8. The method of claim 7 wherein the maintaining step comprises the step of maintaining the covered condition for longer than six hours.

9. A method of prepping the skin of a patient prior to surgery, comprising the steps of:
    covering the skin in the region of the site of surgery with a material retaining a sufficient bactericidal agent to apply the agent to the skin;
    maintaining the skin in the covered condition for a prolonged period of time; and
    removing the retaining material prior to surgery, including the step of applying pressure against the retaining material.

10. A method of prepping the skin of a patient prior to surgery, comprising the steps of:
    covering the skin in the region of the site of surgery with a material retaining a sufficient bactericidal agent to apply the agent to the skin;
    maintaining the skin in the covered condition for a prolonged period of time; and
    removing the retaining material prior to surgery, including the step of raising the skin temperature of the patient beneath the material.

11. A method of prepping the skin of a patient prior to surgery, comprising the steps of:
    covering the skin in the region of the site of surgery with a material retaining a sufficient bactericidal agent to apply the agent to the skin;
    maintaining the skin in the covered condition for a prolonged period of time; and
    removing the retaining material prior to surgery, including the step of hydrating the skin of the patient beneath the material.

12. A method of prepping the skin of a patient prior to surgery, comprising the steps of:
    covering the skin in the region of the site of surgery with a material retaining a sufficient bactericidal agent to apply the agent to the skin;
    maintaining the skin in the covered condition for a prolonged period of time; and
    removing the retaining material prior to surgery, including the step of stimulating the production of sebum and sweat in the patient beneath the material.

13. A method of prepping the skin of a patient prior to surgery, comprising the steps of:
    covering the skin in the region of the site of surgery with a material retaining a sufficient bactericidal agent to apply the agent to the skin;
    maintaining the skin in the covered condition for a prolonged period of time; and removing the retaining material prior to surgery, including the step of providing a liquid and bacteria impervious barrier over the retaining material.

14. A method of prepping the skin of a patient prior to surgery, comprising the steps of:
covering the skin in the region of the site of surgery with a material retaining sufficient bactericidal agent to apply the agent to the skin;
covering the retaining material with liquid and bacteria impervious material being sufficiently elastic to apply pressure against the retaining material while raising the skin temperature, hydrating the skin, stimulating the production of sebum and sweat, and removing the oxygen supply from aerobic bacteria in the patient;
maintaining the skin in the covered condition for longer than six hours; and
removing the retaining and liquid impervious materials prior to surgery.

15. A method of prepping the skin of a patient prior to surgery, comprising the steps of:
wrapping the skin in the region of the site of surgery with an elongated material from a roll retaining sufficient bactericidal agent to apply the agent to the skin;
wrapping the retaining material with an elongated liquid and bacteria impervious material from a roll;
maintaining the skin in the wrapped condition for a prolonged period of time; and
removing the wrapped materials prior to surgery.

16. The method of claim 15 wherein the maintaining step comprises the step of maintaining the wrapped condition for longer than six hours.

17. The method of claim 15 wherein the second wrapping step includes the step of applying pressure by the liquid impervious material against the retaining material.

18. The method of claim 15 wherein the second wrapping step includes the step of adhering the liquid impervious material over the retaining material.

19. A method of prepping the skin of a patient prior to surgery, comprising the steps of:
wrapping the skin in the region of the site of surgery with an elongated material from a roll retaining sufficient bactericidal agent to apply the agent to the skin;
covering the retaining material with a liquid and bacteria impervious material;
maintaining the covered condition for a prolonged period of time; and
removing the materials prior to surgery.

20. The method of claim 19 wherein the maintaining step comprises the step of maintaining the covered condition for 21. The method of claim 19 wherein the covering step includes the step of applying pressure by the liquid impervious material against the retaining material.

22. A method of prepping the skin of a patient prior to surgery, comprising the steps of:
covering the skin in the region of the site of surgery with a material retaining sufficient bactericidal agent to apply the agent to the skin;
wrapping the retaining material with an elongated liquid and bacteria impervious material from a roll;
maintaining the skin in the wrapped condition for a prolonged period of time; and
removing the materials prior to surgery.

23. The method of claim 22 wherein the maintaining step comprises the step of maintaining the wrapped condition for longer than six hours.

24. The method of claim 22 including the step of applying pressure by the liquid and bacteria impervious material against the retaining material.

25. The method of claim 22 including the step of adhering the liquid and bacteria impervious material over the covering material.

26. A method of prepping the skin of a patient prior to surgery, comprising step of:
wrapping an elongated sheet of porous material saturated with a bactericidal agent while providing a liquid and bacteria impervious back surface of the sheet, and while applying pressure by the sheet against the patient's skin; and
removing the liquid and bacteria impervious back surface and porous material prior to surgery.

27. The method of claim 26 including the step of adhering a side portion only of the sheet to a previous turn of the sheet while providing an exposed front surface of the sheet to the skin.

28. A method of prepping the skin of a patient prior to surgery, comprising the steps of:
applying a hollow glove of porous material saturated with a bactericidal agent to the patient's hand and arm; and
applying pressure to the glove while providing the glove with a bacteria and liquid impervious barrier; and
removing the bacteria and liquid impervious barrier and porous material prior to surgery.

29. A method of prepping the skin of a patient prior to surgery, comprising the steps of:
applying a hollow stocking of porous material saturated with a bactericidal agent to the patient's foot and leg; and
applying pressure to the stocking while providing the stocking with a bacteria and liquid impervious barrier; and
removing the bacteria and liquid impervious barrier and porous material prior to surgery.

30. A method of prepping the skin of a patient prior to surgery, comprising the steps of:
applying a hollow glove of porous material saturated with a bactericidal agent to the patient's hand and extending to a location on the arm below the site of surgery;
wrapping an elongated sheet of porous material saturated with a bactericidal agent over the arm from the glove to a location above the site of surgery; and
applying pressure to the glove and wrapped sheet while providing the glove and sheet with a bacteria and liquid impervious barrier; and
removing the bacteria and liquid impervious barrier and porous materials prior to surgery.

31. A method of prepping the skin of a patient prior to surgery, comprising the steps of:
applying a hollow stocking of porous material saturated with a bactericidal agent to the patient's foot and extending to a location on the leg below the site of surgery;
wrapping an elongated sheet of porous material saturated with a bactericidal agent over the leg and extending from the stocking to a location above the site of surgery; and
applying pressure to the stocking and wrapped sheet while providing the stocking and sheet with a bacteria and liquid impervious barrier; and
removing the bacteria and liquid impervious barrier and porous materials prior to surgery.

* * * * *